(12) United States Patent
Koo et al.

(10) Patent No.: US 9,778,374 B2
(45) Date of Patent: Oct. 3, 2017

(54) PHANTOM AND PHANTOM SYSTEM

(71) Applicant: Research & Business Foundation SUNGKYUNKWAN UNIVERSITY, Suwon-si (KR)

(72) Inventors: Jachoon Koo, Seoul (KR); Hyukjin Lee, Changwon-si (KR); Hae Jin Lee, Incheon (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 139 days.

(21) Appl. No.: 14/725,127

(22) Filed: May 29, 2015

(65) Prior Publication Data

US 2015/0346351 A1    Dec. 3, 2015

(30) Foreign Application Priority Data

May 30, 2014   (KR) .................. 10-2014-0065925

(51) Int. Cl.
| | |
|---|---|
| G01T 1/08 | (2006.01) |
| A61B 6/03 | (2006.01) |
| A61B 6/00 | (2006.01) |
| G01T 1/16 | (2006.01) |
| G01T 1/161 | (2006.01) |

(52) U.S. Cl.
CPC ............ G01T 1/08 (2013.01); A61B 6/032 (2013.01); A61B 6/486 (2013.01); A61B 6/50 (2013.01); A61B 6/583 (2013.01); G01T 1/161 (2013.01)

(58) Field of Classification Search
CPC ........ G01T 1/08; G01T 1/161; A61B 6/583; A61B 6/032; A61B 6/486; A61B 6/50

USPC ............ 250/475.2, 252.1; 378/207, 18
See application file for complete search history.

(56) References Cited

U.S. PATENT DOCUMENTS

| | | | | |
|---|---|---|---|---|
| 4,816,762 A | * | 3/1989 | Bohning | G01R 33/58 |
| | | | | 324/300 |
| 5,719,916 A | * | 2/1998 | Nelson | A61B 6/583 |
| | | | | 378/207 |
| 5,805,665 A | * | 9/1998 | Nelson | A61B 6/583 |
| | | | | 378/207 |
| 2004/0060340 A1 | * | 4/2004 | Hibi | G09B 23/286 |
| | | | | 73/1.86 |
| 2005/0227364 A1 | * | 10/2005 | Madsen | A61B 5/055 |
| | | | | 436/80 |
| 2007/0140413 A1 | * | 6/2007 | Saracen | A61B 6/08 |
| | | | | 378/18 |

(Continued)

FOREIGN PATENT DOCUMENTS

| | | |
|---|---|---|
| JP | 2000-089663 A | 3/2000 |
| KR | 10-2010-0047910 A | 5/2010 |
| WO | WO 2014022480 A1 * 2/2014 | ........... A61N 5/1071 |

*Primary Examiner* — David Porta
*Assistant Examiner* — Blake Riddick
(74) *Attorney, Agent, or Firm* — NSIP Law (57) ABSTRACT

Provided herein is a phantom and a phantom system, the phantom including a plurality of blocks combined having different elastic modulus, and thus may be easily manufactured in various shapes, movements, and densities and may exactly imitate movements of a tissue such as in a lung that has high volume change rates and has a high possibility that a position and shape of a tumor may change, thereby providing an effect of being used in replacement of patients when evaluating 4D-CT performance and measuring radiation amounts.

13 Claims, 10 Drawing Sheets

(56) References Cited

U.S. PATENT DOCUMENTS

| | | | |
|---|---|---|---|
| 2008/0298540 A1* | 12/2008 | Serban | A61B 6/583 378/18 |
| 2009/0110140 A1* | 4/2009 | Krautim | A61N 5/1048 378/18 |
| 2010/0167251 A1* | 7/2010 | Boutchko | A61B 5/416 434/267 |
| 2012/0207283 A1* | 8/2012 | Muller | A61B 6/583 378/207 |
| 2016/0278734 A1* | 9/2016 | Hong | A61B 6/583 |

* cited by examiner

PHANTOM AND PHANTOM SYSTEM

CROSS-REFERENCE TO RELATED APPLICATION

This application claims the benefit under 35 USC §119(a) of Korean Patent Application No. 10-2014-0065925, filed on May 30, 2014, in the Korean Intellectual Property Office, the entire disclosure of which is incorporated herein by reference for all purposes.

1. FIELD

The following description relate to a phantom and a phantom system, and to a phantom consisting of a plurality of blocks with different elastic modulus, and a phantom system using the same.

2. BACKGROUND

Changes in people's lifestyles and eating habits due to modernization are leading to increased incidence of various cancers. In line with this trend, medical equipments have advanced so that a human body can be photographed by various newly developed diagnostic apparatuses to make an early diagnosis of cancer and locate the cancer cells, and then to kill the cancer cells using radiation treatment and the like or suppress the propagation of the cancer cells, thereby treating the cancer or alleviating the pain of cancer patients.

However, in the process of developing and manufacturing a new diagnosis apparatus, it is a very dangerous task to actually expose a human body to the diagnosis apparatus in order to check its accuracy or performance.

Therefore, in the process of developing various medical equipments and treatments methods, a phantom is used that is a model of a human body.

There are two types of such phantoms: static model and dynamic model.

Static model phantoms are used in x-rays or 3D-CT and the like. They imitate only the shapes of human bodies and not the movements.

Dynamic model phantoms are configured to imitate not only the shapes of human bodies but also the movements such as in hearts or lungs.

However, conventional phantoms are made in integrated forms, and thus it is time-consuming and cumbersome to manufacture a different phantom for every organ of a human body that may be different in size and shape depending on the person.

Furthermore, since a conventional dynamic model phantom is made of one type of material, the change rates are the same in any position, and thus there is a problem that it cannot imitate the exact movements of an actual lung which has a greater length change rate in the lower part than the lower part during a breathing exercise.

That is, such conventional phantoms have limitations in imitating various human bodies and situations exactly when checking the performance of new equipments such as 4D-CT capable of dynamic image photographing.

Accordingly, the inventors of the present disclosure have come to develop a new type of phantom capable of resolving the limitations of such conventional phantoms.

PRIOR ART DOCUMENTS

Patent Literature (Patent document 1) Korean patent publication no. 10-2010-0067497

(Patent document 2) Korean patent publication no. 10-2007-0118394

SUMMARY

Therefore, a purpose of various embodiments of the present disclosure is to resolve the aforementioned problems of conventional technology, that is, to provide a phantom consisting of a plurality of blocks that can be manufactured quickly in various sizes and shapes.

Another purpose of the various embodiments of the present disclosure is to provide a phantom capable of imitating movements of an actual human organ by arranging suitable blocks having different elastic modulus in different positions.

Another purpose of the various embodiments of the present disclosure is to provide a phantom wherein target blocks are colored in different colors from other blocks so as to represent target cells such as cancer cells in a diagnosis apparatus.

Another purpose of the various embodiments of the present disclosure is to provide a phantom wherein blocks are made of sponge having elasticity and target blocks are formed as elastic bags having plastic pieces so that the target blocks may move naturally as the phantom moves.

Another purpose of the various embodiments of the present disclosure is to provide a phantom capable of exactly imitating movements of a tissue such as in a lung that has high volume change rates and a high possibility that the position and shape of a tumor may change.

Another purpose of the various embodiments of the present disclosure is to provide a phantom wherein blocks having higher elastic modulus are arranged in an upper area than in a lower area so as to exactly imitate movements of a lung.

Another purpose of the various embodiments of the present disclosure is to provide a phantom system having a phantom inside it so that the phantom may exactly imitate movements of a lung as pressure is applied or removed.

An embodiment of the present disclosure provides a phantom including a plurality of blocks combined.

The blocks may be made of material having elasticity, and the phantom may consist of at least two groups, the blocks in each group having elastic modulus different from the blocks of other groups.

An upper area of the phantom may include more blocks having higher elastic modulus than a lower area of the phantom, thereby forming a phantom that may exactly imitate movements of a lung having greater contract and expansion movements in the lower area.

Furthermore, some of the blocks may be target blocks that are shown in a color different from a color of other blocks when photographed with a diagnosis apparatus.

The target blocks may be made of elastic bags including plastic pieces, and the target blocks may be combined with the other blocks as the elastic bags are combined with surrounding blocks, thereby enabling the target blocks to be moved or changed naturally according to the movements of the phantom.

Some of the other blocks may include a means for measuring radiation amount.

Another embodiment of the present disclosure provides an external case having a hollow interior; a pressure adjuster configured to increase or decrease a pressure inside the external case; a phantom which is disposed inside the external case and which comprises a plurality of blocks combined; and an internal film case configured to envelop the phantom such that the phantom is in fluid connection with air outside the external case by means of an air pipe; wherein, in response to a pressure increase inside the external case by the pressure adjuster, a volume of the phantom decreases due to the increased pressure, and in response to a pressure decrease inside the external case by the pressure adjuster, the volume of the phantom increases due to air supplied through the air pipe.

The present disclosure may be manufactured in various sizes and shapes, and has an effect of providing a phantom capable of exactly imitating movements of a moving human organ such as a lung, representing target cells such as cancer cells, and exactly copying movements of the target cells according to movements of the human organ, and a phantom system using the same.

Especially, the present disclosure has an effect of exactly imitating movements of a tissue that has high volume change rates and a high possibility that the shape or position of a tumor may change according to movements of the tissue, and thus may be used as a replacement to patients in evaluating 4D-CT performance, and measuring radiation amounts.

The aforementioned effects of the present invention are not limited to the aforementioned effects, and other effects not mentioned above will be clearly understood by those skilled in the art from the disclosure of the claims.

DETAILED DESCRIPTION

Hereinafter, a phantom and a phantom system according to the present disclosure will be explained in detail with reference to the attached drawings.

In the explanation below, only the parts needed for understanding a phantom and a lung phantom system according to the embodiments of the present disclosure will be explained, and explanation on other parts will be omitted in order not to distract the concepts of the present disclosure.

Furthermore, the terms or words used in the present specification and claims to be explained hereinafter should not be interpreted as being limited to their general lexical meanings, but should be interpreted as meaning the concepts corresponding to the technical ideas of the present disclosure so as to describe the present disclosure most appropriately as possible.

Figure 1:
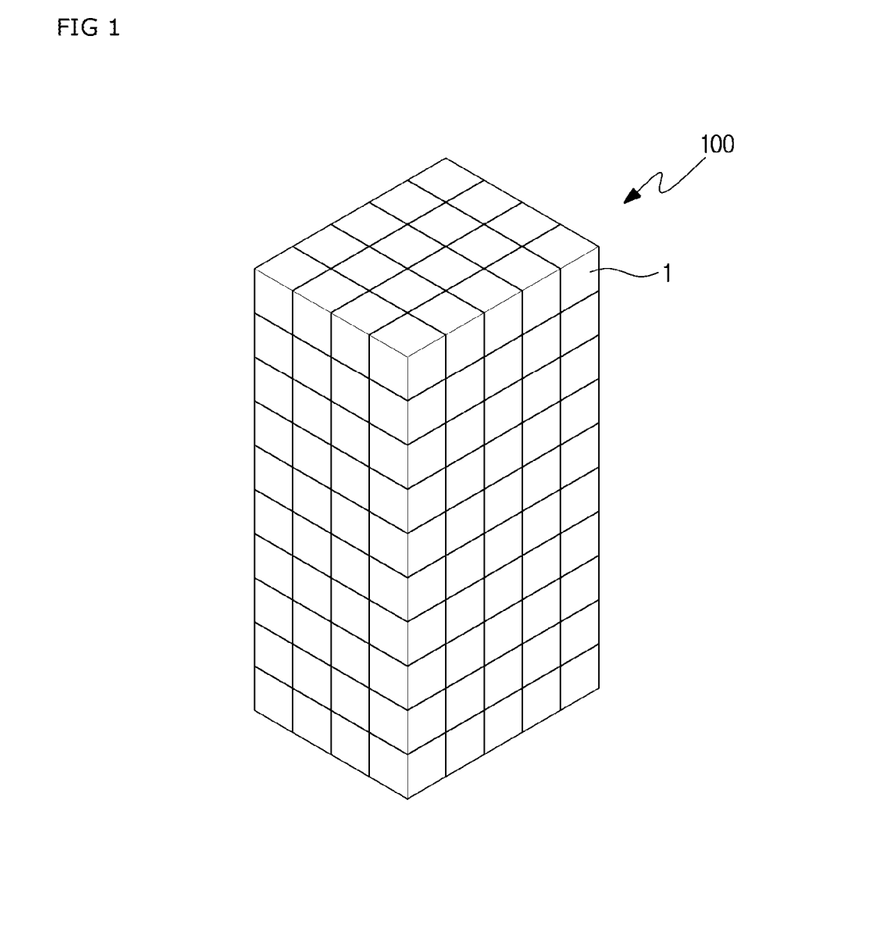
FIG. 1 is a perspective view of a phantom according to a first embodiment of the present disclosure.

FIG. 1 is a perspective view of a phantom according to a first embodiment of the present disclosure.

The phantom according to the present disclosure is formed by combining a plurality of blocks as illustrated in FIG. 1.

More specifically, the phantom 100 according to the first embodiment of the present disclosure is formed by connecting and piling up a plurality of unit blocks 1 using an adhesive. However, the material forming the blocks or the movement of the blocks may be affected by the adhesive used. Therefore, a suitable connecting structure may be used between the blocks instead of an adhesive, wherein the connecting structure may be a structure that allows the connected blocks to be separated from each other.

A unit of the aforementioned blocks may be made of various materials capable of imitating an organ of a human body. Especially, the blocks may desirably be made of materials having elasticity like sponge or latex so that the blocks may imitate movements of the human organ.

Especially, in the case of manufacturing a phantom for a lung for breathing, since the density inside the lung is close to that of air, it is desirable to select a material such as sponge that has a density close to 0 (zero).

Figure 2:
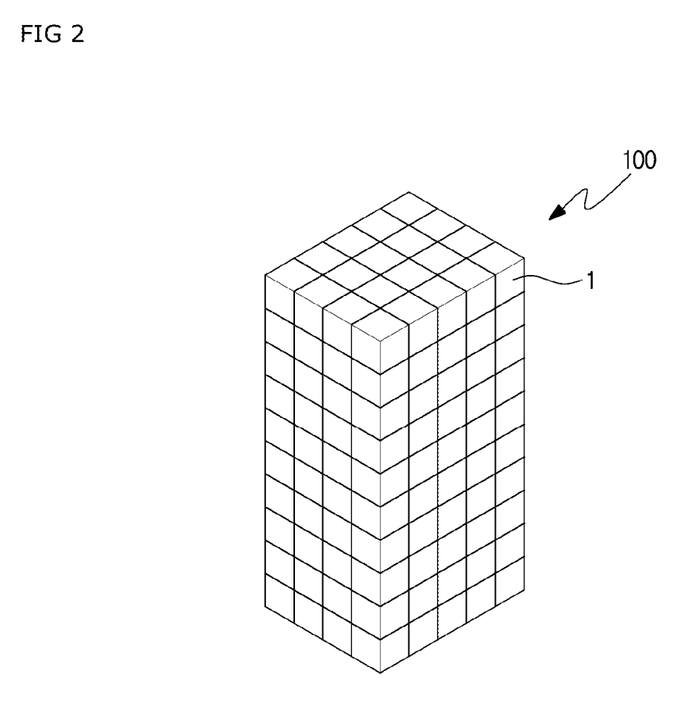
FIG. 2 is a perspective view of a contracted phantom of FIG. 1.

In the case of a unit block 1 manufactured with material having elasticity as aforementioned, when external pressure increases, the unit blocks contract as illustrated in FIG. 2, and when external pressure decreases, the unit blocks expand and be restored as illustrated in FIG. 1, and thus the phantom consisting of these blocks are capable of imitating movements of a human organ.

FIG. 1 illustrates a phantom formed in a rectangular parallelepiped shape using regular hexahedron blocks of a same size in order to easily explain the features of the phantom according to the present disclosure. However, the phantom according to the present disclosure does not have to be made of blocks of the same shape as long as the phantom is made of a plurality of blocks. Furthermore, the shape of the block is not limited to regular hexahedron, that is, blocks of various shapes may be used. The shape of the phantom may also be configured differently depending on the shape of the organ of the human body intended to be represented.

As such, since the phantom according to the embodiment of the present disclosure is formed by combining a plurality of blocks, it is possible to form the phantom in various sizes and shapes by arranging a suitable number of blocks and connecting the blocks according to the size and shape of the human organ.

Figure 3:
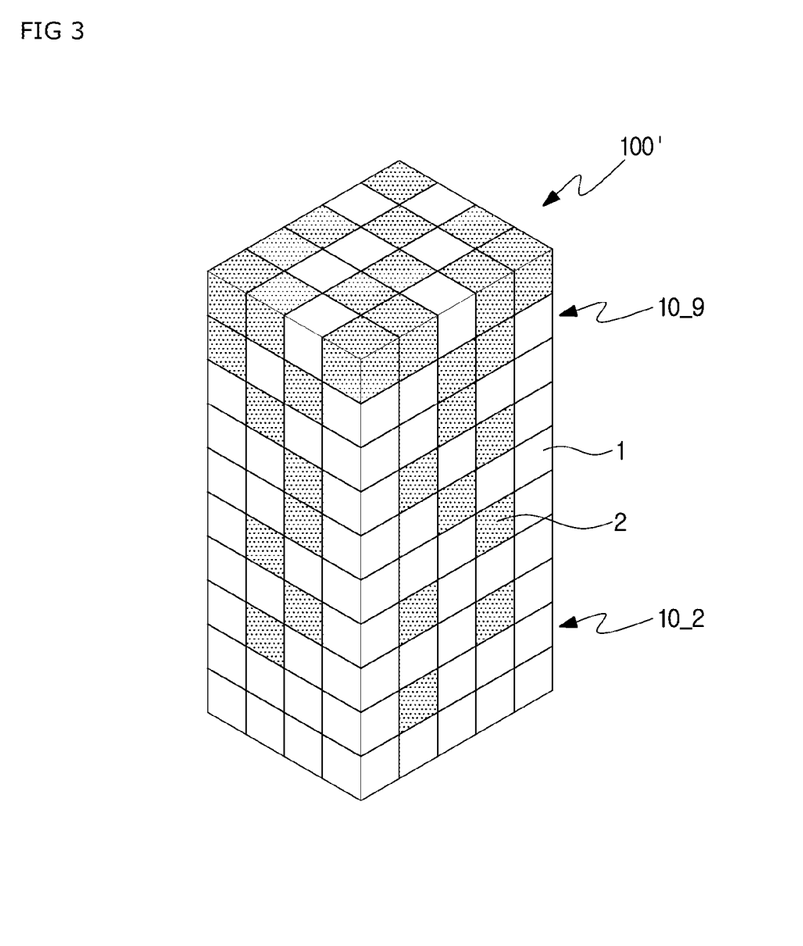
FIG. 3 is a perspective view of a phantom according to a second embodiment of the present disclosure.

FIG. 3 illustrates a perspective view of a phantom according to a second embodiment of the present disclosure.

The phantom according to the second embodiment of the present disclosure is formed using a plurality of blocks as in the phantom of the first embodiment. However, unlike the first embodiment, the phantom according to the second embodiment is formed using blocks having different elastic modulus.

More specifically, the phantom according to the second embodiment of the present disclosure is formed using at least two groups of blocks.

For example, assuming the phantom is formed using two groups of blocks, the elastic modulus of the blocks 2 in group B is higher than the elastic modulus of the blocks 1 in group A. That is, assuming the blocks are made of sponge, the sponge blocks 2 of group B are firmer than the blocks 1 of group A, and thus when a same pressure is applied to the two groups of blocks, the blocks 2 of group B contract less than the blocks 1 of group A, whereas the blocks 1 of group A contract more than the blocks 2 of group B when the pressure increases and expand more than the blocks 2 of group B when the pressure decreases.

As such, by using blocks having different elastic modulus, it is possible to easily configure a phantom imitating an organ of a human body with different tissue density.

Furthermore, it can be seen from movements of a human organ such as a lung that the amount of change in an upper area and the amount of change in a lower area are different depending on breathing. That is, when air is breathed in and the lung expands, the lower area expands more than the upper area, and when air is breathed out and the lung contracts, the lower of the lung contracts more than the upper area of the lung.

Therefore, in order to imitate such a lung, it is desirable to form the upper area of the phantom with a material having a higher elastic modulus than the lower area.

Figure 4A:
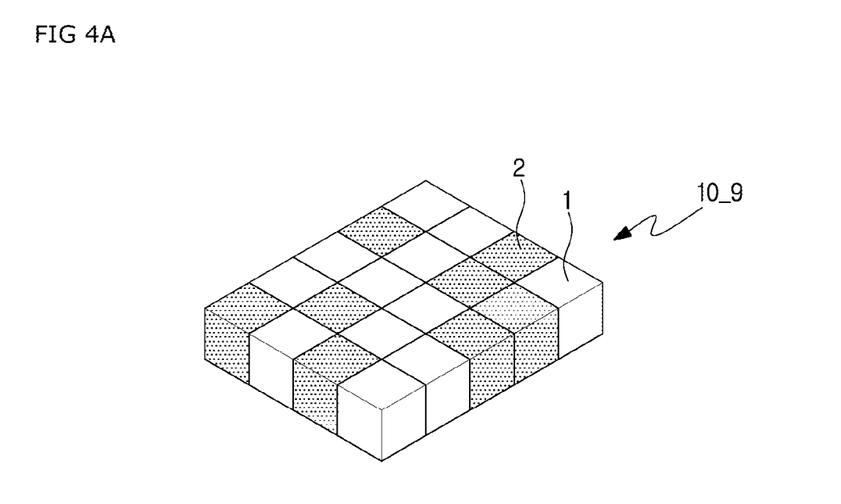
FIG. 4A is a perspective view of a configuration of some block layers in an upper area of the phantom illustrated in FIG. 3.
Figure 4B:
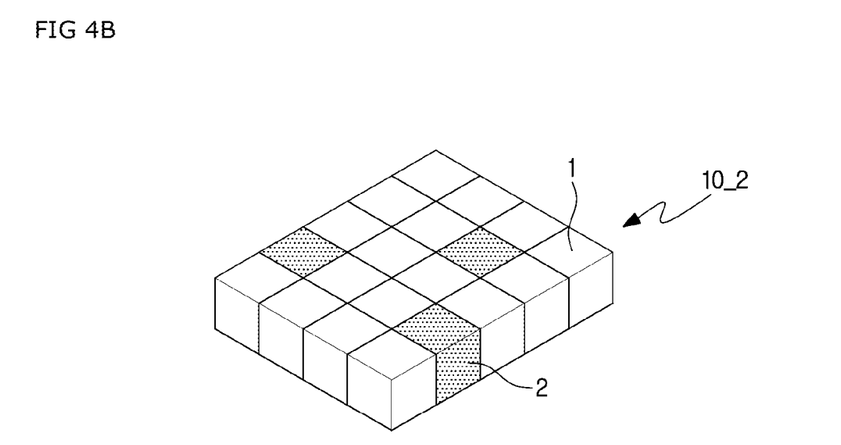
FIG. 4B is a perspective view of a configuration of some block layers in a lower area of the phantom illustrated in FIG. 3.

More specifically, when forming a phantom using blocks having different elastic modulus, it is possible to arrange blocks in such a manner that an upper layer 10_9 has more blocks having higher elastic modulus than a lower layer 10_2 as illustrated in FIGS. 4A and 4B so that the lower area may expand and contract more than the upper area.

Figure 5:
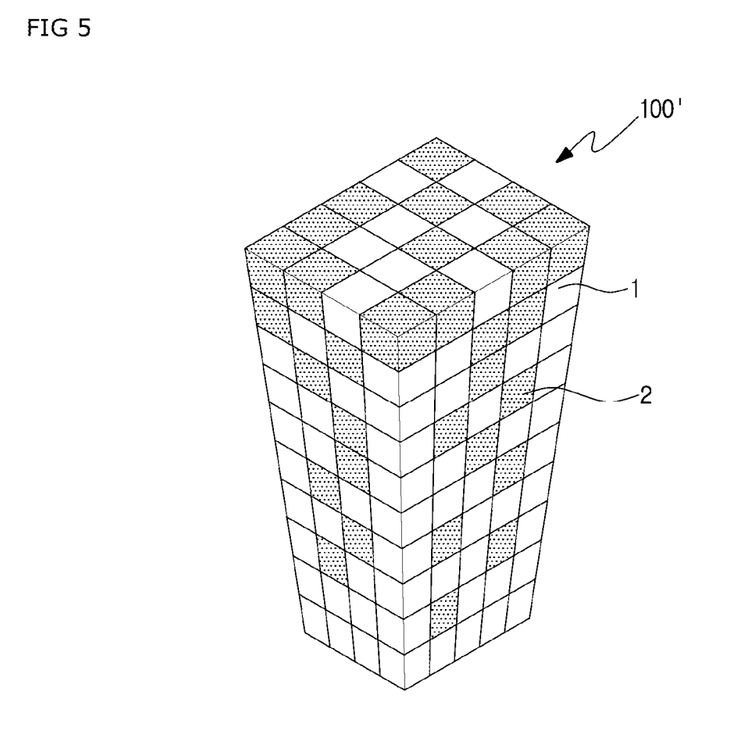
FIG. 5 is a perspective view of a contracted phantom of FIG. 3.

When configured as above, in the phantom having the shape of FIG. 3, the lower area contracts more as shown in FIG. 5 when a pressure is applied, and expands and is restored as shown in FIG. 3 when the pressure is decreased again, thereby appropriately imitating movements of the lung when breathing.

Figure 6:
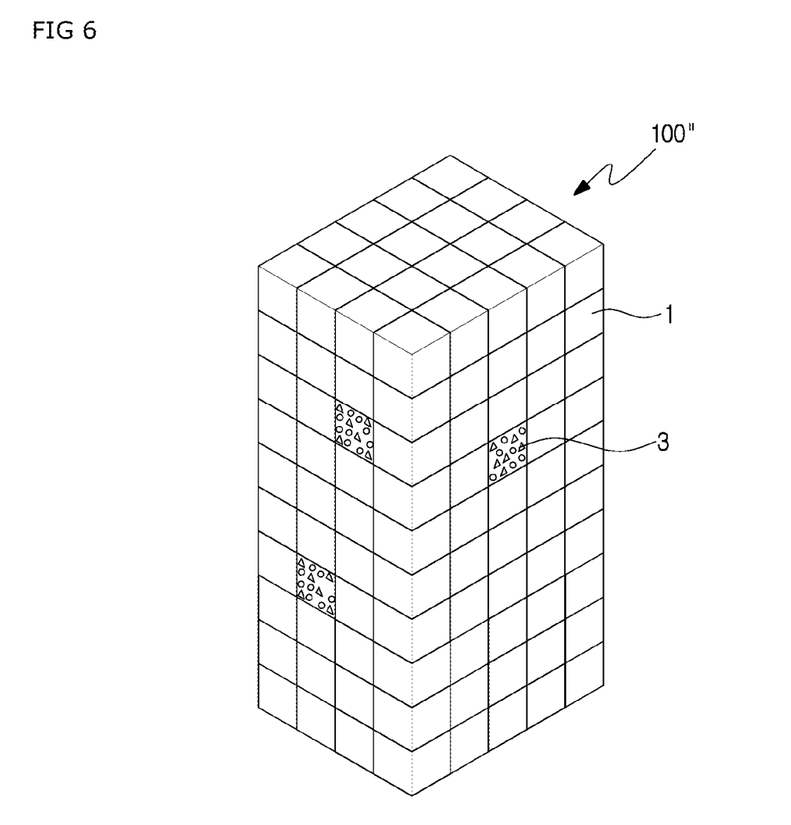
FIG. 6 is a perspective view of a phantom according to a third embodiment of the present disclosure.

FIG. 6 is a perspective view of a phantom according to a third embodiment of the present disclosure.

The phantom 100" according to the third embodiment of the present disclosure is formed using a plurality of blocks just as the phantoms of the first embodiment and the second embodiment. However, unlike the first embodiment and the second embodiment, the phantom 100" of the third embodiment is characterized to include target blocks 3. Furthermore, the phantom 100" according to the third embodiment may be configured to have only the blocks with a same elastic modulus as in the first embodiment, or configured to have blocks of two or more groups having different elastic modulus as in the second embodiment.

The target blocks 3 are blocks representing target cells or a tissue such as cancer cells that must be found in a human organ. These target blocks should be shown in different colors from other blocks in an image photographed by a diagnosis apparatus such as ultrasound wave and CT so that their location can be identified.

For this purpose, unlike the other blocks made of sponge or latex, the target blocks may be made of plastic material.

However, when an entirety of the target blocks are made of plastic material that has no elasticity, it is not possible to exactly imitate a tissue such as cancer cells that move naturally according to movements of human tissues.

Figure 7:
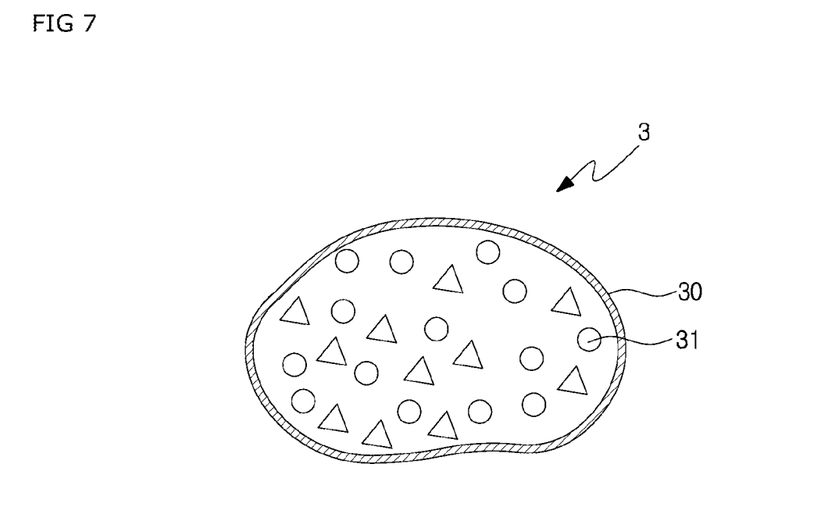
FIG. 7 is a cross-sectional view of a configuration of a target block.

Therefore, in the present disclosure, the target blocks 3 consist of elastic bags 30 like sand bags that contain plastic pieces 31 inside. The elastic bags 30 of the target blocks 3 are made of material having elasticity such as latex, and the plastic pieces 31 inside the elastic bags 30 may have various shapes.

Figure 8A:
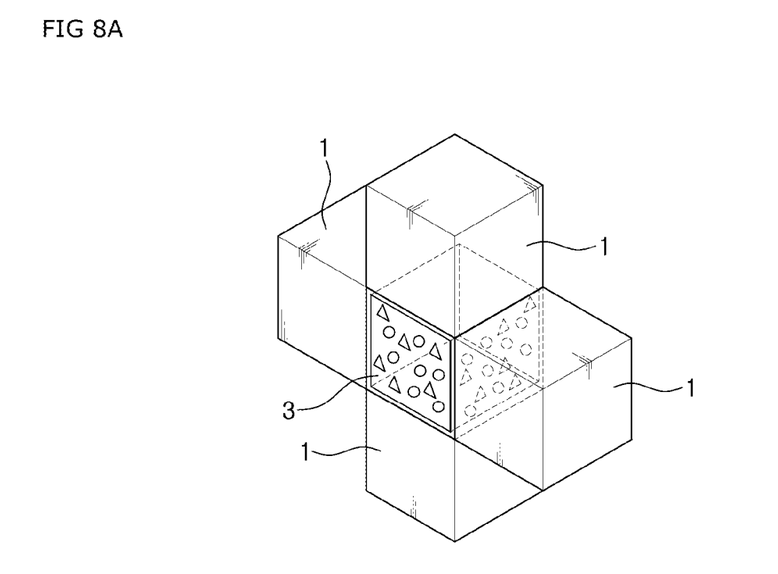
FIGS. 8A and 8B are views for illustrating a connection relationship and movement between a target block and normal blocks.
Figure 8B:
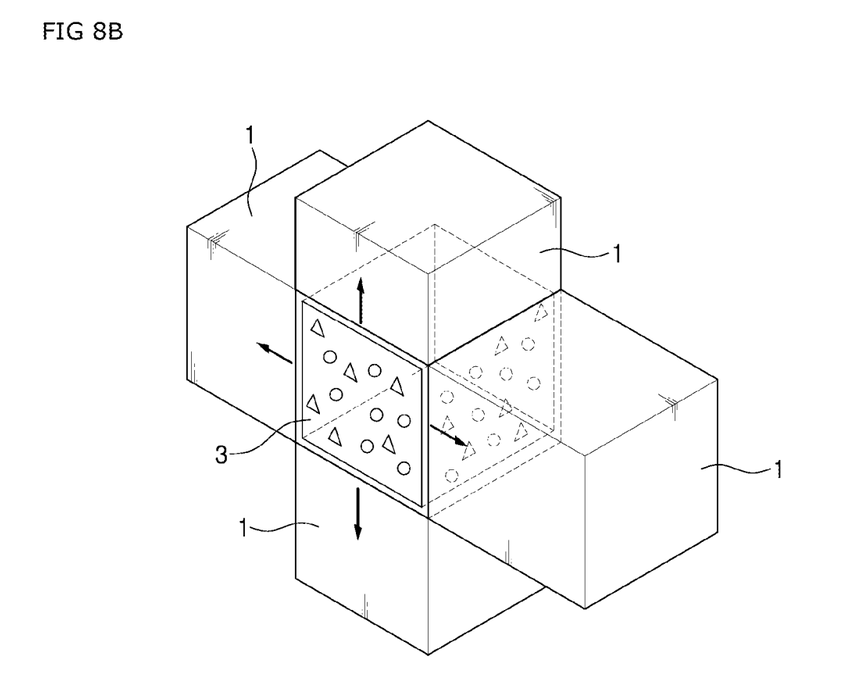

When the elastic bags 30 are combined with surfaces of the other blocks 1 surrounding the target blocks and thus the surrounding blocks 1 expand or contract as illustrated in FIGS. 8A and 8B, the target blocks may also expand or contract naturally.

Therefore, the present disclosure can be effectively used in replacement of patients when evaluating 4D-CT performance and measuring radiation amount since it can exactly imitate movements of a tissue that has high volume change rates and that has a high possibility that the position and shape of a tumor may change.

Figure 9:
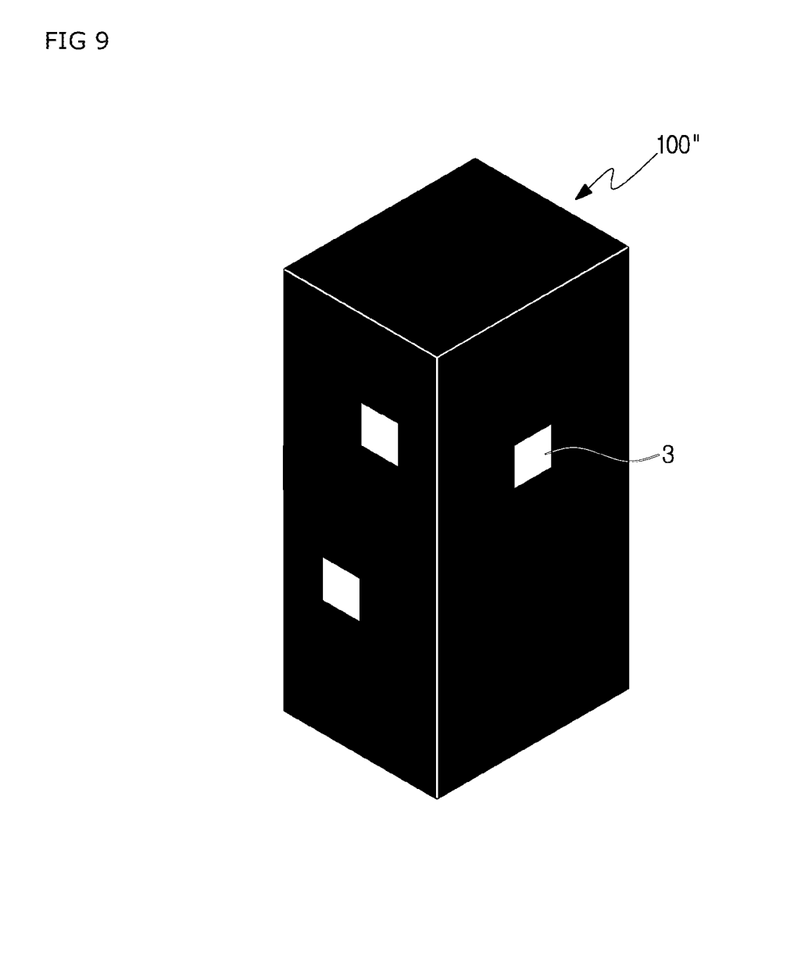
FIG. 9 is an exemplary view of an image of the phantom of FIG. 6 photographed by a diagnosis apparatus.
Figure 10:
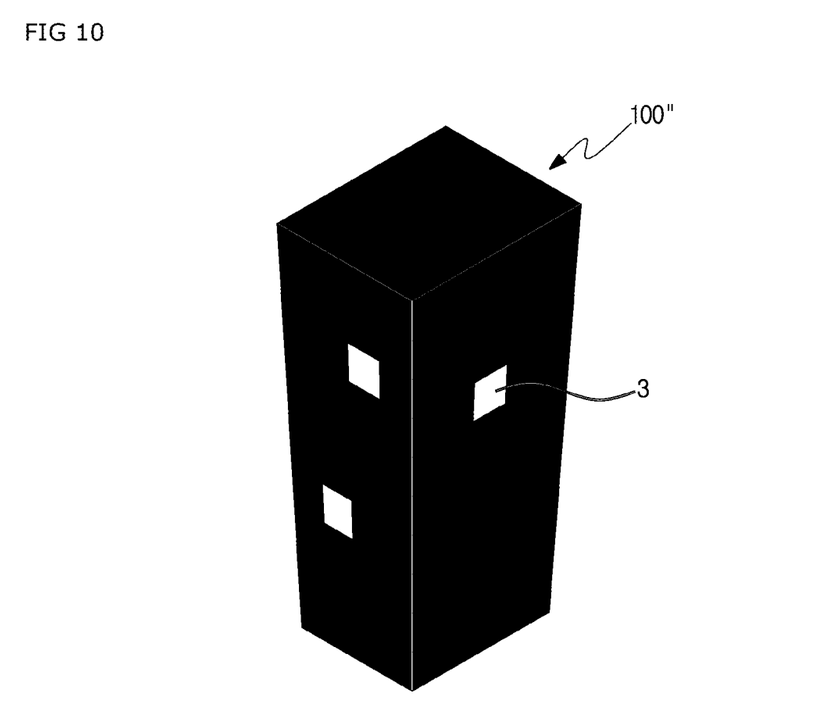
FIG. 10 is an exemplary view of an image of the contracted phantom of FIG. 6 photographed by a diagnosis apparatus.

By photographing the phantom 100" according to the third embodiment of the present disclosure illustrated in FIG. 6 with a diagnosis apparatus, the location of the target blocks 3 are confirmed as illustrated in FIG. 9, and when the phantom moves due to external pressure, the target blocks 3 also move naturally as illustrated in FIG. 10, and the moved location may be checked from the photographed image of the diagnosis apparatus.

When using the phantom according to the third embodiment of the present disclosure, it is possible to identify in real time the movements of a tumor that moves according to breathing motion etc., and based on these movements, it is possible to develop radiation treatments that follow the tumor.

Furthermore, by inserting into the other blocks 1 a tool for measuring radiation amount, it is possible to identify how much radiation was emitted to the other blocks that are normal cells, after emitting radiation to the target tumor.

The tool for measuring radiation amount is not illustrated in the drawings, but it may consist of for example an ion chamber to be attached to surfaces of the other blocks, and the amount of radiation emitted to the blocks may be calculated after measuring the amount of radiation collected in the ion chamber after emitting radiation.

This may be helpful in calculating the amount of radiation when treating patients.

The phantoms according to the embodiments of the present disclosure explained so far can be manufactured easily and quickly in various shapes and configurations. Furthermore, the phantoms according to the present disclosure are capable of imitating movements of a human tissue where movements of each area are not consistent, that is, where expansion and contraction are not consistent such as in for example a lung.

Figure 11A:
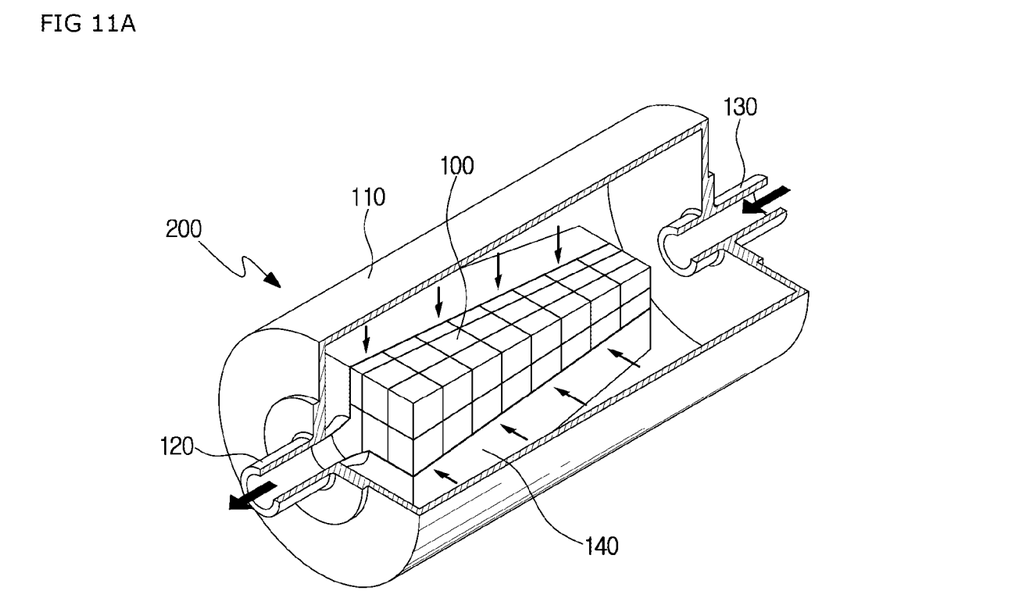
FIG. 11A is a partial cut open view illustrating a phantom contracting due to changes in pressure in a phantom system according to an embodiment of the present disclosure.
Figure 11B:
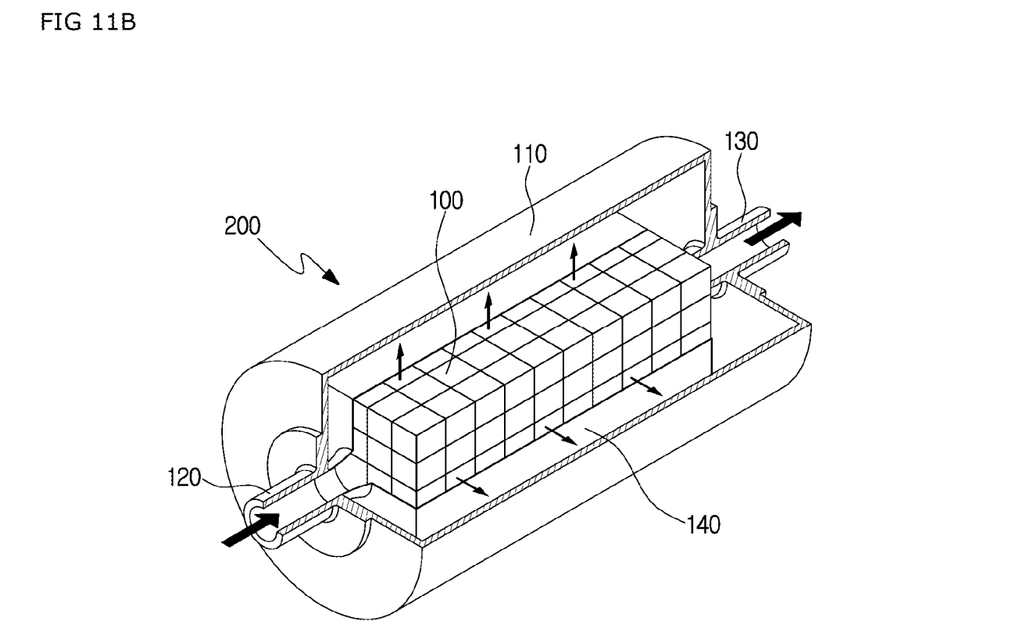
FIG. 11B is a partial cut open view illustrating a phantom expanding due to changes in pressure in a phantom system according to an embodiment of the present disclosure.

A phantom system for enabling a phantom of the present disclosure to represent expansion/contraction movements is illustrated in FIG. 11.

As illustrated in FIG. 11, the phantom system according to an embodiment of the present disclosure includes an external case 110, a pressure adjuster 120 configured to increase/decrease pressure inside the external case, a phantom according to an embodiment of the present disclosure positioned inside the external case, and an internal film case 140 which envelops the phantom such that the phantom is in fluid connection with air outside of the external case through an air pipe 130.

The external case 110 is a case which has a hollow interior, and the interior of the external case 110 may be filled with water or air, and the internal pressure may be increased or decreased by the water or air injected or discharged from the pressure adjuster.

The phantom 100 of an embodiment of the present disclosure is positioned inside such an external case, and the phantom 100 is enveloped by the internal film case 140 such as vinyl so that the water or air inside the external case does not infiltrate directly into the phantom 100.

Furthermore, the internal film case 140 is connected to the air pipe 130 so that the phantom can be in fluid connection with the air outside the external case 110, as illustrated in FIGS. 11A and 11B.

In such a phantom system according to the embodiment of the present disclosure, water or air pressure is injected by the pressure adjuster 120 as illustrated in FIG. 11A, so that when the pressure inside the external case increases, the increased pressure pressurizes the phantom 100, in which case the air inside the phantom would be discharged outside through the air pipe 130, thereby decreasing the volume of the phantom as the volume of the blocks forming the phantom decreases.

Then, when the water or air pressure is discharged outside the external case by the pressure adjuster 120, the internal pressure of the external case would decrease, and accordingly, outside air would be injected into the internal film case 140 through the air pipe 130, and the volume of the blocks forming the phantom 110 would expand together with the phantom as illustrated in FIG. 11B.

As the contraction state illustrated in FIG. 11A and the expansion state illustrated in FIG. 11b are repeated, the phantom inside imitates movement of a lung that repeats contraction and expansion.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

EXPLANATION ON REFERENCE NUMERALS 1, 2: BLOCK
3: TARGET BLOCK
10: BLOCK LAYER
31: ELASTIC BAG
32: PLASTIC PIECES
100, 100', 100": PHANTOM
110: EXTERNAL CASE
120: PRESSURE ADJUSTER
130: AIR PIPE
140: INTERNAL FILM CASE
200: PHANTOM SYSTEM

What is claimed is:

1. A phantom comprising,
a plurality of blocks combined into a continuous body having a first region and a second region; and
a deformable target block incorporated into the continuous body, the deformable target block being made of an elastic bag including plastic pieces,
wherein the plurality of blocks comprises at least two groups, the blocks in each group having an elastic modulus different from that of the blocks of other groups,
wherein the first region comprises more blocks having a higher elastic modulus than the second region does, so that the first region and the second region are configured to differentially contract under an identical pressure.

2. The phantom according to claim 1,
wherein the deformable target block exhibits a color different from a color of the plurality of blocks when photographed with a diagnosis apparatus.

3. The phantom according to claim 1,
wherein some of the plurality of blocks are configured to measure a radiation amount.

4. The phantom according to claim 1,
wherein the phantom comprises a plurality of deformable target blocks.

5. The phantom according to claim 4,
wherein the plurality of deformable target blocks is configured to mimic a shape or movement of a tumor.

6. The phantom according to claim 1,
wherein the deformable target block is configured to aggregate or disperse the plastic pieces relative to each other in proportion to deformation of blocks adjacent to the deformable target block.

7. A phantom system comprising:
an external case having a hollow interior;
a pressure adjuster configured to increase or decrease a pressure inside the external case;
a phantom which is disposed inside the external case and which comprises
a plurality of blocks combined into a continuous body having a first region and a second region; and
a deformable target block incorporated into the continuous body, the deformable target block being made of an elastic bag including plastic pieces,
wherein the plurality of blocks comprises at least two groups, the blocks in each group having an elastic modulus different from that of the blocks of other groups,
wherein the first region comprises more blocks having a hi her elastic modulus than the second region does, so that the first region and the second region are configured to differentially contract under an identical pressure; and
an internal film case configured to envelop the phantom such that the phantom is in fluid connection with air outside the external case by an air pipe;
wherein, in response to a pressure increase inside the external case by the pressure adjuster, a volume of the phantom decreases due to the increased pressure, and in response to a pressure decrease inside the external case by the pressure adjuster, the volume of the phantom increases due to air supplied through the air pipe.

8. The phantom system according to claim 7,
wherein the deformable target block exhibits a color different from a color of the plurality of blocks when photographed with a diagnosis apparatus.

9. The phantom system according to claim 7,
wherein some of the plurality of blocks are configured to measure a radiation amount.

10. The phantom system according to claim 7,
wherein the phantom comprises a plurality of deformable target blocks.

11. The phantom system according to claim 10,
wherein the plurality of deformable target blocks is configured to mimic a shape or movement of a tumor.

12. The phantom system according to claim 7,
wherein the phantom imitates a shape of a lung.

13. The phantom according to claim 7,
wherein the deformable target block is configured to aggregate or disperse the plastic pieces relative to each other in proportion to deformation of blocks adjacent to the deformable target block.

\* \* \* \* \*